(12) United States Patent
Mansson et al.

(10) Patent No.: US 9,150,894 B2
(45) Date of Patent: Oct. 6, 2015

(54) PROCESS FOR PURIFYING LIPOPEPTIDES

(75) Inventors: Martin Mansson, Oslo (NO); Eli Karin Dale, Oslo (NO); Sissel Hauge, Oslo (NO); Carsten Overballe-Petersen, Hvidovre (DK); Kjersti Aastorp Hirth, Oslo (NO); Dennis Brian Hansen, Rodovre (DK)

(73) Assignee: XELLIA PHARMACEUTICALS APS (DK)

( * ) Notice: Subject to any disclaimer, the term of this patent is extended or adjusted under 35 U.S.C. 154(b) by 362 days.

(21) Appl. No.: 12/708,539

(22) Filed: Feb. 19, 2010

(65) Prior Publication Data
US 2010/0228006 A1    Sep. 9, 2010

Related U.S. Application Data
(60) Provisional application No. 61/153,660, filed on Feb. 19, 2009.

(51) Int. Cl.
*C07K 1/36* (2006.01)
*C12P 17/18* (2006.01)
*C12P 21/02* (2006.01)

(52) U.S. Cl.
CPC .............. *C12P 17/188* (2013.01); *C07K 1/36* (2013.01); *C12P 21/02* (2013.01)

(58) Field of Classification Search
None
See application file for complete search history.

(56) References Cited

U.S. PATENT DOCUMENTS

| | | |
|---|---|---|
| 4,537,717 A | 8/1985 | Abbott et al. |
| 4,874,843 A | 10/1989 | Baker |
| 4,885,243 A | 12/1989 | Huber et al. |
| 6,696,412 B1 | 2/2004 | Kelleher et al. |
| RE39,071 E | 4/2006 | Baker et al. |
| 8,697,638 B2 | 4/2014 | Keith et al. |
| 8,796,224 B2 | 8/2014 | Keith et al. |
| 8,846,610 B2 | 9/2014 | Keith et al. |
| 2007/0191280 A1 | 8/2007 | Kelleher et al. |
| 2008/0253992 A1* | 10/2008 | DeFrees et al. .............. 424/85.2 |

FOREIGN PATENT DOCUMENTS

| | | |
|---|---|---|
| WO | 0256829 A2 | 7/2002 |
| WO | 2009144739 A1 | 12/2009 |

OTHER PUBLICATIONS http://www.chemie.uni-hamburg.de/bc/praktika/skripte/HIC.pdf as cited on May 2, 2012.*
JP11503733A cited in JP application 2011-551028 Office Action of Jul. 1, 2014.
JP4193894A cited in JP application 2011-551028 Office Action of Jul. 1, 2014.
JP8506023A cited in JP application 2011-551028 Office Action of Jul. 1, 2014.
"II Chromatography" from Protein Purification-Principles, High Resolution Methods, and Applications; Jan-Christer Janson and Lars Ryden editors; ISBN 0-89573-122-3; pp. 175-223, (1989).
Gu, et al.; "Structural Characterization of Daptomycin Analogues A21978C1-3(d-Asn11) Produced by a Recombinant Streptomyces Roseosporus Strain"; J. Nat. Prod.; 70; pp. 233-240; (2007).
International Preliminary Report on Patentability; International Application No. PCT/NO2010/000066; International Filing Date Feb. 19, 2010; date of Mailing Sep. 1, 2011; 4 pages.
International Search Report; International Application No. PCT/NO2010/000066; International Filing Date Feb. 19, 2010; date of mailing Jun. 18, 2010; 3 pages.
Written Opinion of the International Searching Authority; International Application No. PCT/NO2010/000066; International Filing Date Feb. 19, 2010; 3 pages; date of mailing Aug. 19, 2011.

* cited by examiner

*Primary Examiner* — Robert A Wax
*Assistant Examiner* — Jessica Worsham
(74) *Attorney, Agent, or Firm* — Cantor Colburn LLP

(57) ABSTRACT

The present invention relates to a process for purifying lipopeptides. More particular, the invention provides an improved method for purifying daptomycin.

17 Claims, No Drawings

PROCESS FOR PURIFYING LIPOPEPTIDES

This application claims the benefit under 35 USC §119 to U.S. provisional patent application 61/153,660 filed 19 Feb. 2009.

FIELD OF THE INVENTION

The present invention relates to an improved purification process for the purification of daptomycin represented by the chemical name N-decanoyl-L-tryptophyl-D-asparaginyl-L-aspartyl-L-threonylglycyl-L-ornithyl-L-aspartyl-D-alanyl-L-aspartylglycyl-D-seryl-threo-3-methyl-L-glutamyl-3-anthraniloyl-L-alanine ε1-lactone. Daptomycin can be presented by the formula I:

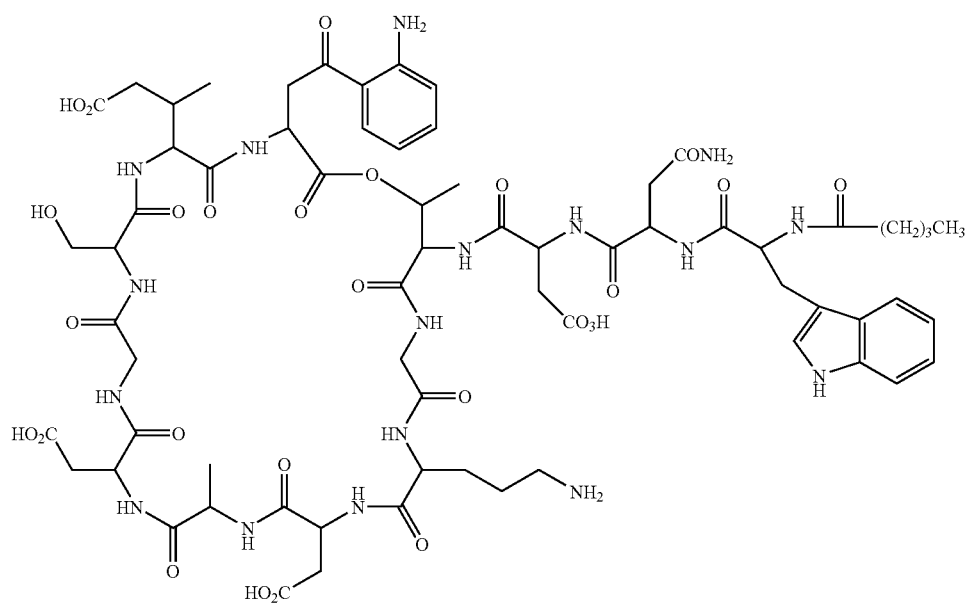

(I)

BACKGROUND

Daptomycin is a lipopeptide antibiotic with activity against gram-positive organisms. Daptomycin is produced by fermentation of *Strepromyces roseosporus* and then purification of the fermentation broth. The mechanism of action for daptomycin is that it binds to bacterial membranes and causes a rapid depolarization of the membrane potential. This loss of membrane potential causes inhibition of protein, DNA and RNA synthesis, resulting in bacterial cell death. Daptomycin is approved for complicated skin and skin structure infections (cSSSI) and *Staphylococcus aureus* bloodstream infections (bacteraemia). Daptomycin is marketed by Cubist Pharmaceuticals under the trademark CUBICIN®.

Daptomycin was first described in the mid 1980's in several patents and journals; U.S. Pat. No. 4,537,717 and Debono M. et al, Journal of Antibiotics, 1986, Vol. XL, No 6, 761-777. Since then there have been several publications regarding improved fermentation processes and purification processes.

In U.S. Pat. No. 4,885,243 an improved fermentation process for making daptomycin is described. This method describes the feeding of decanoic fatty acid or ester or salts thereof to a fermentation broth of *Strepromyces roseosporus*. During fermentation, the decanoic fatty acid will be inserted to the molecule to form the decanoic side chain of daptomycin.

In the prior art, several purification processes for purifying daptomycin has been described. U.S. Pat. No. 4,874,843 describes a method for purifying daptomycin in which the fermentation broth was filtered and added to a chromatographic column containing Diaion® HP-20 styrene-divinyl-benzene resin for hydrophobic compounds. After elution, the semipurified daptomycin was passed through a column containing Diaion® HP-20ss resin and then added to another column containing Diaion® HP-20 resin, a directly polymerized small particle size version of HP-20. In addition to these steps, attempts to increase the purity with several additional chromatographic steps without any success are described. The '843 patent further teach that by using a non-functional resin and an aqueous solution and including a step where water are physically removed and then rewet the resin with a polar organic solvent, the purity of the product is increased from 80% to 93%. This process is time consuming and not very well suitable for industrial production.

The U.S. RE 39,071 patent describes the two major impurities found in the production of daptomycin, the anhydro-daptomycin and the beta-isomer of daptomycin. The U.S. RE 39,071 further states that by using the method described in example 1-3 you will have a daptomycin product comprising less than 6% of the two mentioned impurities. Example 3 describes a method where intermediate quality of daptomycin is further purified in a method comprising four chromatographic steps and additional desalting, concentration and freeze drying steps. In the chromatographic steps acetonitrile is used for washing and elution and in addition you have to perform the method with chilled solutions and in a chilled room.

U.S. Pat. No. 6,696,412 patent disclose a method for purifying daptomycin by utilizing an anion exchange chromatography step where a modified buffer is used for elution and by utilizing a microfiltration step where daptomycin forms micelles. There are several methods described in this patent that is a combination of the two steps mentioned above in combination with other purification steps familiar to the person skilled in the art. The highly purified daptomycin product is defined in the patent to be daptomycin with a purity level of 95-97%.

SUMMARY OF THE INVENTION

The present invention provides for an improved purification method for purifying daptomycin that result in a product with a purity of at least 95%. The described method is simpler than those methods described in the prior art and as described below it renders superfluous the use of modified buffers and avoids the use of acetonitrile which is a benefit to the environment.

The method according to the invention utilizes the steps of anion exchange chromatography and reverse phase chromatography. In addition, normal filtration steps and lyophilisation of the final product may be performed.

According to one embodiment, the monovalent salt solution used as elution buffer in the anion exchange chromatographic steps is a solution of sodium chloride in water.

The elution buffer of the reverse phase chromatographic step b) of the present invention is aqueous alcohol. Preferably, the aqueous alcohol is aqueous ethanol. According to one embodiment of the present invention, daptomycin is eluted from the reverse phase chromatographic step using an elution buffer comprising 40-70% ethanol in water.

The present invention can be illustrated by the steps given in the reaction scheme 1.

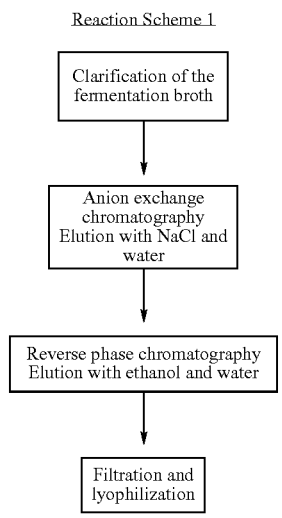

Reaction Scheme 1

The present invention results in a daptomycin product with a total purity of 95% or more. The amount of the anhydro-daptomycin varies between 0.5-1.5% and the amount of the beta-isomer is less than 0.5%.

The method according to this invention provides a purification method that is simpler than methods known in the art with respect to the buffers and steps used, it avoids the use of solvents that are toxic to the environment. In addition, it results in a very good separation and low levels of the two most important impurities; anhydro-daptomycin and the beta-isomer of daptomycin. The method according to the invention gives a simple purification process while providing a product that is at least as pure as products described in the prior art.

DETAILED DESCRIPTION OF THE INVENTION

The starting material of the process according to the present invention can be made by the method described in U.S. Pat. No. 4,885,243 where the fatty acid to be fed is decanoic acid.

According to the present invention, daptomycin is purified by the use of a first anion chromatography step, and a following second reverse phase chromatography step.

The fermentation broth used as a starting material of the present invention may be pre-treated before said chromatography steps to remove large particles and biomass. As a pre-treatment method, the fermentation broth used as a starting material of the present invention may be passed through one or more clarification steps. Various useful clarification steps are known to the person skill in the art. Non-limiting examples of clarification steps useful to pre-treat the fermentation broth according to the present invention is reverse osmosis, centrifugation, ultrafiltration, microfiltration, nanofiltration, and diafiltration. Even an anion exchange step with a highly porous resin is possible to utilize for clarification.

It is to be understood that various combination of clarification methods well known to the skilled person may be used according to the present invention to pre-treat the fermentation broth before further purification of daptomycin by anion change chromatography and reverse phase chromatography.

The clarified fermentation broth is added to an anion exchange column. Both strong anion exchanger resins such as Capto Q (high-flow agrose strong anion exchange resin produced by GE Healthcare), Q Sepharose™ XL (highly cross-linked agarose ion exchange resin produced by GE Healthcare), Q Sepharose™ FF (highly cross-linked agarose fast flow ion exchange resin produced by GE Healthcare), Source™ 15 Q (polystyrene/divinylbenzene anion exchange resin produced by GE Healthcare), Source™ 30 Q Q (polystyrene/divinylbenzene anion exchange resin produced by GE Healthcare)or Macroprep® High Q (rigid methacrylate strong anion exchange resin produced by Bio-Rad), or equivalents and also weak anion exchanger resins, such as the commercial available resins DEAE Sepharose™ FF (cross-linked agarose ion exchange resin produced by GE Healthcare), ANX Sepharose™ FF (crosslinked agarose ion exchange resin produced by GE Healthcare), Source™ 15 Q may be used according to the present invention. The preferred resin is a highly cross-linked agarose resin with dextran surface extender, like the commercial available resin Capto Q. After loading of the clarified solution, the column is washed with water.

The elution buffer of the anion exchange chromatography step a) of the present method is a monovalent salt solution. Said monovalent salt may e.g. be a chloride salt such as NaCl or KCl. Other monovalent salts may also be used such as monovalent salts of acetate, such as sodium acetate.

According to one embodiment, daptomycin may be eluted from the column with a NaCl gradient in water with the gradient going from 0.1 M NaCl to 1.5M NaCl, preferably going from 0.2M NaCl to 1.0M NaCl.

The semi-purified daptomycin is then added to a reversed phase column. The preferred reverse phase resin is a mono-sized, porous resin made of polystyrene and divinyl benzene, like the commercial available resin Source™ RPC 30 (polystyrene/divinyl benzene resin produced by GE Healthcare, Sepabeads® SP20ss (small particle size styrenic resin), Diaion® HP20ss or equivalent polystyrene based resin types. After the daptomycin solution has been applied the column, the column is washed with water containing 15% of alcohol, such as 15% ethanol.

The daptomycin may be eluted with an aqueous alcohol, e.g. a C1-C3 alkyl alcohol, such as methanol, ethanol or isopropanol. According to one embodiment of the present invention, daptomycin is eluted from a reversed phase column using ethanol as the eluting solvent.

Daptomycin is according to one embodiment eluted from the reverse phase column by a gradient of ethanol in water. The gradient is from 5-80% ethanol and preferably from 40%-70% of ethanol.

In one preferred embodiment of the invention there is an additional step of reverse phase chromatography. A preferred embodiment of the invention is to run the two reverse phase columns on different pH to improve the purity of the product. In one preferred embodiment the first column is run at neutral pH and the second column is run at acidic pH. It is not essential which order the two reverse phase chromatography steps are run in respect of pH. The first column may be run at acidic pH and the second at neutral pH or vice versa.

According to one embodiment of the invention, the first reverse phase chromatography column is eluted at pH 6.5-8.5, preferably at pH 7.5-8.0. According to another embodiment of the invention, the second reverse phase chromatography column is eluted at pH 2.5-3.5, preferable at pH 3.0-3.1.

The column to be used in the reverse phase chromatography step in the method according to the present invention may be a styrene based resin such as the commercial available resin Source™ 30RPC. Other equivalent reverse phase chromatography resins, such as Sepabeads® SP20ss, Diaion® HP20ss or equivalent polystyrene based resin types known to the skilled person may also be used.

The purified daptomycin is then filtered and lyophilized under standard conditions. The final purified daptomycin has a purity of at least 95%.

EXPERIMENTAL

Example 1

After clarification the partly purified daptomycin solution was loaded on an anion exchange column. The starting material was clarified by diafiltration.

Purification on Ion Exchange Chromatography:

Diafiltrated daptomycin was loaded onto an anion exchanger column, Capto Q resin.

Buffers were prepared in separate tanks with the following composition:
Buffer 1: DI-water
Buffer 2: 0.2 M NaCl
Buffer 3: 0.4 M NaCl
Buffer 4: 1.0 M NaCl The starting solution was adjusted to pH 6-8 with a diluted NaOH prior to loading. The daptomycin was bound to the resin at a maximum capacity of 20 g/L resin. After binding to the resin, fermentation related impurities were washed out initially with buffer 1 then followed by buffer 2.

Elution and recovery of daptomycin was conducted isocratic with buffer 3. After elution the column was stripped with buffer 4 to remove any remaining daptomycin or strong binding impurities.

The daptomycin was collected based on a volume app. 5-10 BV

Reverse Phase Chromatography I (RPC I):

The daptomycin was purified by HPLC using a styrene based Source™ 30RPC resin

Buffers for the step were prepared in separate tanks:
Buffer 1: DI-water
Buffer 2: 12-16% ethanol
Buffer 3: 55-65% ethanol Daptomycin was purified at neutral pH (pH 7.5-8.0). Initially the column was equilibrated with buffer 1. The daptomycin was loaded onto the column (maximum loading degree <30 g/L resin) before less hydrophobic impurities were washed out (mainly degradation products) using buffer 2.

Daptomycin was then recovered by gradient elution 15 to 60% ethanol (gradient mixing of buffer 1 to 2) over 12-16 BV. The daptomycin was collected based on UV signal.

Reverse Phase Chromatography II:

Based on purity, fractions were collected and pooled from the first reverse phase chromatography step (RPC I) and pH was adjusted to pH 3.0-3.1 with acetic acid under fast stirring in order to prevent precipitation of the daptomycin in the tank.

Buffers for this step were prepared in separate tanks:
Buffer 1: DI-water, pH 3.0-3.1 was adjusted with acetic acid
Buffer 2: 30-35% ethanol, pH 3.0-3.1 was adjusted with acetic acid
Buffer 3: 65-75% ethanol, pH 3.0-3.1 was adjusted with acetic acid pH adjusted daptomycin solution was loaded onto the column (maximum loading degree <30 g/L resin) and less hydrophobic impurities were washed out with buffer 1. Elution and recovery of the daptomycin was conducted by running an ethanol gradient from 35% to 70% mixing buffer 2 and 3 over 8-12 BV.

The daptomycin was collected based on UV-signal.

Example 2

To clarify the fermentation broth, several clarification methods was used. Firstly, the fermentation broth was centrifuged in order to remove large particles and biomass. The pH in the fermentation broth was 6.4 and the dry material (DM) was about 6-7%. After centrifugation the supernatant contained only 3% DM. The supernatant was then further prefiltrated through a 25-100 µm filter in order to remove particles larger than 25-100 µm.

The centrifuged and pre-filtered solution was then ultrafiltrated through a Pellicon® 2, 500 kD (Millipore) filter to remove large molecules. After ultrafiltration the solution was up-concentrated by nanofiltration. The filter used was DL-series, 350D (GE Osmonics). The retentate contained 5 g/l of daptomycin and had a pH of 6.

The retentate was further purified by an anion exchange chromatography column according to the present invention. The resin used was Capto Q (90 µm) from GE Healthcare. The pH in the retentate was adjusted to pH 6 with NaOH if needed before it was loaded on to the column. After the retentate was loaded on to the column, the column was washed with water and the daptomycin was eluted with a NaCl step gradient. The elution solutions contained 0.2M, 0.4M and 1.0M NaCl in water. The pooled fractions from the anion exchange column contained about 2.5 g/l of daptomycin.

The pooled fractions from the anion exchange column was then loaded into the first reverse phase chromatography (RPC I). The resin used was Source™ 30RPC (30 µm) from GE Healthcare. After loading the column was washed with water and eluted with a gradient of 20-50% ethanol at pH 7-8. The fractionation pool from this step contained about 6 g/l of daptomycin.

This fractionation pool was further loaded into a second reverse phase column with the same resin. After loading the daptomycin solution from the previous reversed phase column, the column was washed with water and daptomycin was eluted with a gradient of 20-50% ethanol at pH 3.0. The fractionation pool from this step contains about 8 g/l of daptomycin.

The daptomycin solution was then processed through a nanofiltration step with a DL-series, 350D membrane from GE Osmonics.

After nanofiltration the daptomycin solution was lyophilized using standard conditions.

The purity of the final product is in the range of 95-97%.

The invention claimed is:

1. A process for purifying daptomycin comprising
   a) loading a solution comprising partly purified daptomycin onto an anion exchange chromatography column and eluting a first eluate with a first elution buffer; wherein the partially purified daptomycin is optionally clarified from a fermentation broth comprising daptomycin using one or several clarification steps;
   b) loading the first eluate of step a) onto a first reverse phase chromatography column and eluting a second eluate with a second elution buffer having a pH of 6.5-8.5;
   c) loading the second eluate of step b) onto a second reverse phase chromatography column and eluting a third eluate with a third elution buffer having a pH of 2.5-3.5; and
   d) optionally filtering and lyophilizing the third eluate;
   wherein the first elution buffer in a) is a monovalent salt solution, the second elution buffer in b) consists of water and an alcohol, and the third elution buffer in c) consists of water, an alcohol and an acid.

2. A process according to of claim 1, wherein a purified daptomycin product of the reverse phase chromatography step c) is further purified by one or more filtration steps to produce a filtered product.

3. A process according to claim 2, wherein the filtered product is subjected to a lyophilisation step to produce a lyophilized product.

4. A process according to claim 1, wherein the salt of the monovalent salt solution of the first elution buffer in a) is NaCl.

5. A process according to claim 4, wherein the first elution buffer is 0.1-1.5 M NaCl.

6. A process according to claim 1, wherein the second elution buffer in b) is aqueous ethanol.

7. A process according to claim 6, wherein the second elution buffer is 5-80% ethanol.

8. A process according to claim 1, wherein the anion exchange chromatography step is performed using a highly cross-linked agarose resin with dextran surface extender.

9. A process according to claim 1, wherein the first reverse phase chromatography step is performed using a styrene based resin column.

10. A process according to claim 1, wherein the first reverse phase chromatography column is eluted at pH 7.5-8.0.

11. A process according to claim 1, wherein the second reverse phase chromatography column is eluted at pH 3.0-3.1.

12. A process for purifying daptomycin, consisting of
   a) subjecting a fermentation broth comprising daptomycin to one or several clarification steps to produce a solution;
   b) loading the solution of step a) onto an anion exchange chromatography column and eluting a first eluate with a first elution buffer;
   c) loading the first eluate of step b) onto a first reverse phase chromatography column and eluting a second eluate with a second elution buffer having a pH of 6.5-8.5;
   d) loading the second eluate of step c) onto a second reverse phase chromatography column and eluting a third eluate with a third elution buffer having a pH of 2.5-3.5;
   e) subjecting the third eluate of step d) to one or several filtration steps to produce a filtrate; and
   f) subjecting the filtrate to lyophilisation; producing a purified powder of daptomycin;
   wherein the first elution buffer in b) is a monovalent salt solution,
   and wherein the second elution buffer consists of an alcohol and water, and the third elution buffer consists of water, an alcohol and an acid.

13. A process according to claim 12, wherein the clarification steps in a) are selected from the group consisting of reverse osmosis, centrifugation, filtration, ultrafiltration, nanofiltration, anion exchange chromatography, and combinations thereof.

14. A process according to claim 12, wherein the salt of the monovalent salt solution of the first elution buffer in b) is NaCl.

15. A process according to claim 14, wherein the first elution buffer is 0.1-1.5 M NaCl.

16. A process according to claim 12, wherein the second elution buffer in c) is aqueous ethanol.

17. A process according to claim 16, wherein the second elution buffer is 5-80% ethanol.

* * * * *